United States Patent
Schleicher

(10) Patent No.: US 6,216,268 B1
(45) Date of Patent: Apr. 17, 2001

(54) ELBOW PROTECTION DEVICE AND METHOD FOR APPLYING SAME

(75) Inventor: Thomas R. Schleicher, Chicago, IL (US)

(73) Assignee: SMR Products, Inc., Northbrook, IL (US)

( * ) Notice: Subject to any disclaimer, the term of this patent is extended or adjusted under 35 U.S.C. 154(b) by 0 days.

(21) Appl. No.: 09/493,597

(22) Filed: Jan. 31, 2000

(51) Int. Cl.$^7$ .............................. A41D 13/08; A61F 13/06
(52) U.S. Cl. ............................. 2/16; 128/881; 128/892; 602/62
(58) Field of Search ................................... 2/455, 22, 24, 2/16; 128/881, 878, 892; 602/20, 26, 61, 62

(56) References Cited

U.S. PATENT DOCUMENTS

| | | | |
|---|---|---|---|
| 2,550,461 | * 4/1951 | Fick ............................................. | 2/16 |
| 3,458,867 | * 8/1969 | Moore et al. ................................ | 2/16 |
| 4,198,708 | * 4/1980 | Fugere et al. ............................... | 2/16 |
| 4,315,504 | 2/1982 | Drennan et al. . | |
| 5,123,113 | * 6/1992 | Smith ........................................ | 2/455 |
| 5,168,576 | * 12/1992 | Krent et al. ................................ | 2/455 |
| 5,687,422 | * 11/1997 | Wurst et al. ................................ | 2/24 |
| 5,887,277 | 3/1999 | Lohman . | |
| 5,891,079 | * 4/1999 | Barnes ....................................... | 602/61 |

* cited by examiner

*Primary Examiner*—John J. Calvert
*Assistant Examiner*—Tejash Patel
(74) *Attorney, Agent, or Firm*—Foley & Lardner

(57) ABSTRACT

An elbow protection device for an elbow of a bed patient includes a body having a base, first and second elevation pads connected to the base, respectively, and a strap connected to the device and configured to secure the body to the elbow. A covering is connected to an outer surface of the body, the covering including a friction reducing material for permitting free sliding movement of the device over the bed surface with minimal resistance. The elbow protection device is made of a flexible, compressible, breathable foam material, the body including an inner surface having a plurality of flat areas spaced apart from each other in two dimensions by a plurality of dimples extending into the body from the flat areas, and a strap connected to the body and configured to secure the body to the elbow. The elbow protection device may be applied to a bed patient's elbow by sliding a body of the device under the elbow of the bed patient, placing the bed patient's elbow on the first and second elevation pads, aligning the elbow with the opening within a body and the first and second elevation pads, grasping a first end of a strap, the strap connected to the body at a second end, wrapping the strap around the elbow, and releasably connecting the strap to the body.

31 Claims, 2 Drawing Sheets

ELBOW PROTECTION DEVICE AND METHOD FOR APPLYING SAME

FIELD OF THE INVENTION

The present invention relates generally to the field of medical devices for the prevention and treatment of ulcers suffered by bed patients. More particularly, the invention relates to an elbow protection device for bed patients that prevents contact with bed linens or other objects thereby preventing elbow ulcers or treating existing elbow ulcers.

BACKGROUND OF THE INVENTION

Elbow protection devices for bed patients to prevent ulcers of the elbow are known. Persons who are confined to a bed for an extended period of time may develop ulcers, specifically decubitus ulcers, of the elbow. The primary causes of elbow ulcers are pressure exerted on the elbow of the bed patient from the weight of the patient's arm when the arm is resting in an extended or semi-extended position, and friction and shear resulting from the sliding movement of the patient's elbow across a bed surface. Elbow protection devices typically include an elbow support pad having inwardly extending full convolutions and peaks. The elbow protection devices typically a fixed amount of base support padding under the patient's elbow. Elbow protection devices also typically include tubular sleeves upon which the support pad is attached. The sleeves are typically supplied in more than one size to accommodate the varying sizes of bed patient's arms.

Existing elbow protection devices, however, have a number of drawbacks. The padding with inwardly extending full convolution include a plurality of complete amplitude peaks and valleys. The padding with inwardly extending convolutions and peaks can not be used on all patients. In particular, edematous patient's may be unable to comfortably use the devices without negatively affecting the patient's circulation or irritating the patient's swollen tissue. Also, a fixed amount of base support padding, often either a fixed single layer or a fixed double layer, does not provide sufficient flexibility for supporting the elbow of all patients. A larger patient with a larger or heavier elbow may require additional base padding support than a smaller sized patient with a smaller, lighter elbow. Also, the tubular sleeve must be pulled over the patient's arm to correctly position the device. The installation of the tubular sleeve can interfere with other medical devices such as dressings and intravenous (IV) lines attached to a patient arm at or below the elbow. The installation of the tubular sleeve may require IV lines to be removed and reattached to the patient. Also, the tubular sleeve often covers the entire elbow and a portion of the patient's forearm and upper arm limiting the accessibility of the patient's arm for IV lines, drug injections, and other medical procedures. Moreover, the pulling of the tubular sleeve may cause pain and discomfort to some patients. Once applied, the patient may find the tubular sleeve to be restricting and uncomfortable. The tubular sleeves can be difficult to align and have a tendency to move out of position, particularly following movement of the patient's elbow, thereby not providing proper support to the patient's elbow. The tubular sleeves must be designed and stocked in multiple sizes in order to accommodate the different sized arms of the patients in a hospital, nursing home, or care center.

Accordingly, it would be advantageous to provide an elbow protection device that overcomes these and other disadvantages of existing elbow protection devices. In particular, it would be advantageous to provide an elbow protection device having at least one support pad without full convolutions and inwardly extending peaks that can be worn by all patients including edematous patients. What is needed is an elbow protection device having an additional support pad for supporting patient's with larger or heavier elbows. What is also needed is an elbow protection device for bed patients that can be applied without having to be pulled up a patient's arm. It would also be advantageous to provide an elbow protection device for bed patient's that adjusts to fit all patients. What is also needed is an elbow protection device for bed patients that correctly positions, cradles and suspends the patient's elbow above the bed surface. Further, it would be advantageous to provide an elbow protection device for bed patients that allows for full flexing of the patient's arm without causing the elbow protection device to become misaligned.

SUMMARY OF THE INVENTION

The present invention provides an elbow protection device for an elbow of a bed patient. The elbow protection device includes a body having first and second side panels connected to and spaced apart by a base having a forearm section and an upper arm section, the base being made of a flexible, compressible material, first and second elevation pads connected to the fore arm and upper arm sections, respectively, the base and the first and second elevation pads configured to support the elbow above a bed surface, and an attachment strap connected to the body and configured to secure the body to the elbow.

According to another aspect of the invention, an elbow protection device includes a covering connected to an outer surface of the body, the covering including a friction reducing material for permitting free sliding movement of the device over the bed surface with minimal resistance.

According to another aspect of the invention, an elbow protection includes a body being made of a flexible, compressible, breathable foam material, the body including an inner surface having a plurality of flat areas spaced apart from each other in two dimensions by a plurality of dimples extending into the body from the flat areas, the body contoured to receive the elbow and configured to support the elbow above a bed surface.

The present invention of a heel protection boot, in operation, provides sliding a body of the device under the elbow of the bed patient, placing the bed patient's elbow on first and second elevation pads connected to an inner surface of the body, aligning the elbow with an opening within a body of the device and the first and second elevation pads, grasping a first end of a strap, the strap connected to the body at a second end, wrapping the strap around the elbow, and releasably connecting the strap to the body.

BRIEF DESCRIPTION OF THE DRAWINGS

The invention will become more fully understood from the following detailed description, taken in conjunction with the accompanying drawings, wherein like reference numerals refer to like parts, in which.

DETAILED DESCRIPTION OF THE PREFERRED EMBODIMENTS

Figure 1:
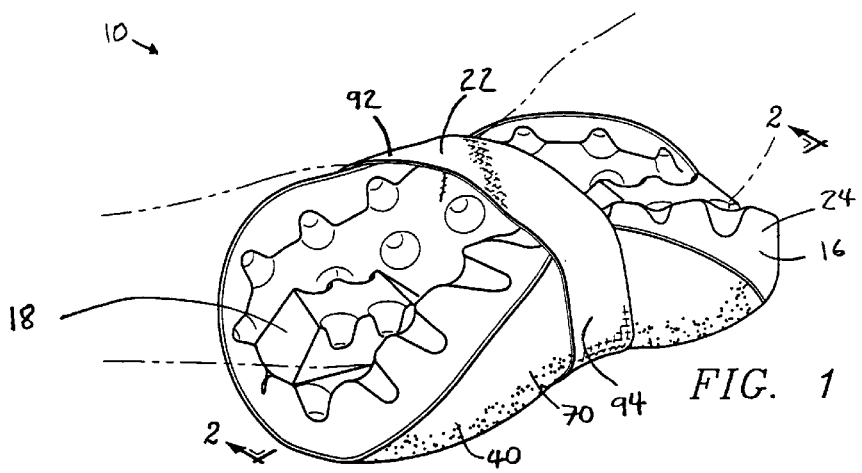
FIG. 1 is a perspective view of an elbow protective device in accordance with an exemplary embodiment of the present invention.

Referring to FIG. 1, an elbow protection device indicated generally at 10 for bed patients that prevents contact with bed linens or other objects of a bed surface 12 thereby preventing elbow ulcers or treating existing elbow ulcers is shown. Device 10 generally includes a body 16, first and second elevation pads 18, 20, a strap 22 and the auxiliary support pad 14. Body 10 comprises a single piece of soft, flexible, compressible and resilient material 24 having an inner surface 26. Inner surface 26 of body 10 includes a plurality of flat areas spaced apart from each other in two dimensions by a plurality of dimples extending into the body from the flat areas resulting in inner surface 26 having a dimpled, flat-face 28. Dimpled, flat-face 28 permits air ventilation within a patient's elbow 30 and body 32, while providing a soft, flat inner surface without peaks that may harm or irritate some patients, particularly edematous patients. Material 24 is made of an open-celled, breathable, non-latex, non-allergenic, medical grade foam, such as polyurethane. In an exemplary embodiment, foam is 1.25 inches thick throughout body 10. The gripping action of material 24 assists in securely holding elbow 30 in a properly supported position. Body 10 is a generally flat circular disk contoured to cradle and support elbow 30 of the bed patient while allowing for full contraction and extension of elbow 30. In an exemplary embodiment, body 10 is a circular disk having a diameter of 13 inches. Body 10 further comprises first and second side panels 32, 34, a base 36 and a covering 40.

Figure 3:
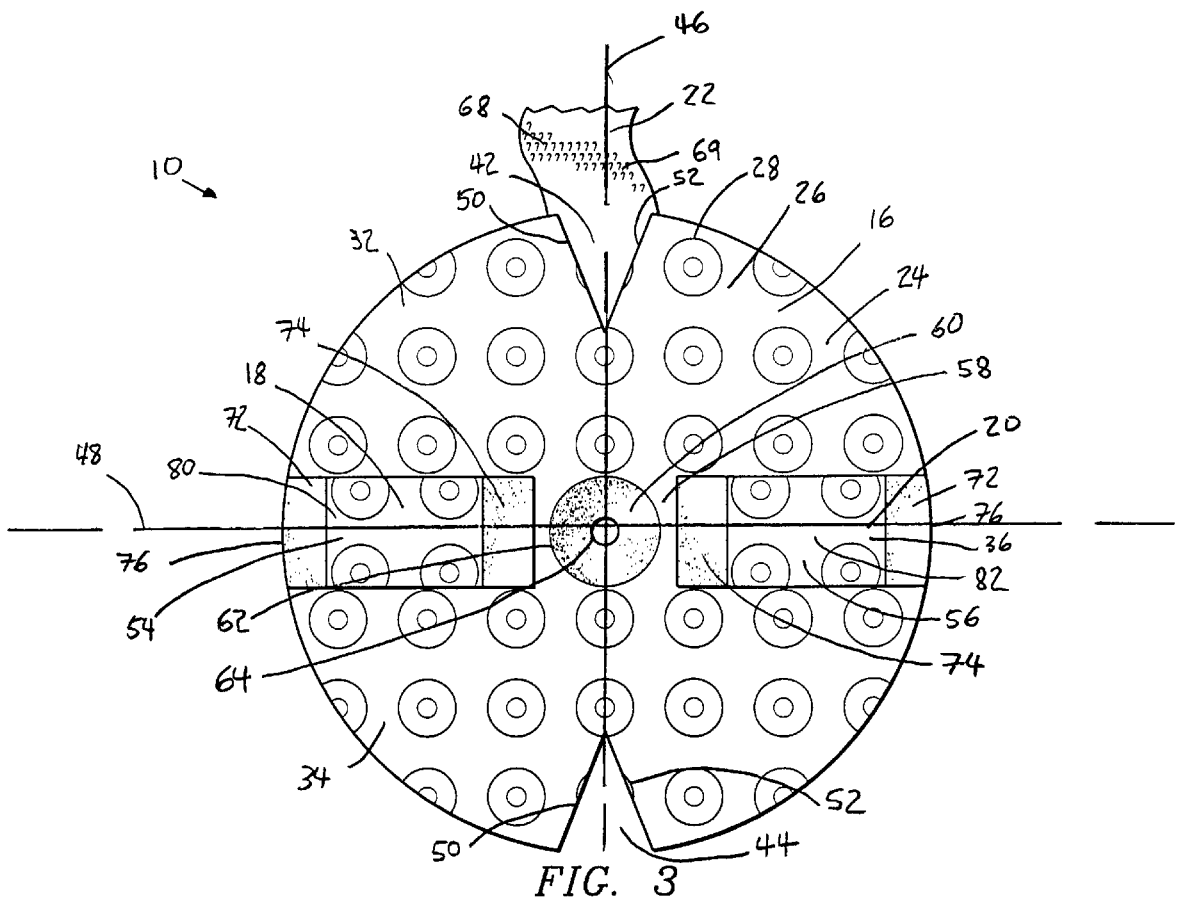
FIG. 3 is top view of the elbow protective device of FIG. 1 in an open position with the first and second cutouts open.

Referring to FIGS. 1 and 3, first and second side panels 32, 34 are generally, semi-circular. First and second side panels 32, 34 are spaced apart by and laterally extend from opposing edges of base 36. First and second side panels 32, 34 include first and second cutouts 42, 44, respectively. In an exemplary embodiment, first and second cutouts 42, 44 are opposing triangular shaped wedges that are positioned along a transverse axis 46 of body 10 and are symmetrical about a longitudinal axis 48 and transverse axis 46 of body 10. Each cutout 42, 44 leaving first and second cutout edges 50, 52 that are sewn together to provide a contoured shape to body 10. Alternative fastening means for fastening first and second cutout edges 50, 52 of first and second cutouts 42, 44 such as gluing, taping, clamping, etc. and alternative cutout shapes such as arcuate, semicircular, etc. are contemplated. In an alternative exemplary embodiment, first and second side panels 32, 34 are pre-formed in a contoured shape.

Figure 2:
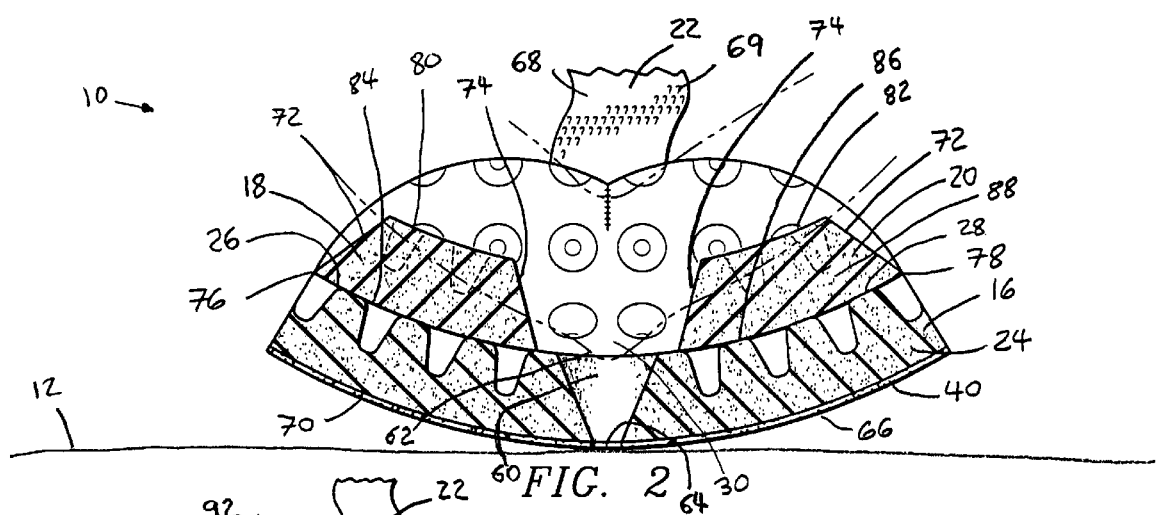
FIG. 2 is a longitudinal cross-sectional view of the elbow protective device taken substantially along lines 2—2 of FIG. 1.

Referring to FIGS. 2 and 3, base 36 is a longitudinal segment connecting first and second side panels 32, 34 and configured to conform to and support the bed patient's protruding side of elbow 30, upper forearm and lower portion of the upper arm. Base 36 further includes an upper arm section 54, a forearm section 56 and an intermediate portion 58. Upper arm and forearm sections 54, 56 are spaced apart by intermediate portion 58 and support the forearm and the upper arm of the bed patient, respectively. Intermediate portion 58 includes an opening 60, having a conical shape, tapered from a first area 62 across inner surface 26 of body 10 to a smaller second area 64 across an outer surface 66 of body 10, wherein first area 62 is larger than second area 64. Opening 60 is configured to receive and to provide annular support to a portion of elbow 30. Other opening configurations such as tapered rectangular, tapered oval, tapered triangular etc. are contemplated. In an alternative exemplary embodiment, opening 60 only partially extends into body 10.

Figure 4:
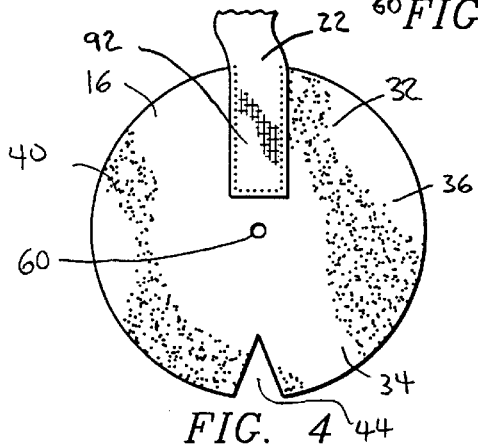
FIG. 4 is a bottom view of the elbow protective device of FIG. 1 with the first and second cutouts open.

Referring to FIGS. 1 and 4, covering 40 comprises a generally circular, flat layer of friction reducing material 70 connected to outer surface 66 of body 10. In an exemplary embodiment, friction reducing material 70 is a Velcro™-like pile or loop material. In an exemplary embodiment, Velcro™-like loop material 70 is stitched to outer surface 66. Other fastening arrangements, such as gluing, taping, heat bonding, etc. are contemplated. Covering 40 stabilizes body 10 when body 10 is moved along bed surface 12 and prevents body 10 from buckling along transverse axis 46 or longitudinal axis 48 of body 10 while still allowing for complete extension and contraction of a patient's arm.

Referring to FIGS. 1 through 3, first and second elevation pads 18, 20 are generally rectangular, flat layers of padding. First elevation pad 18 is stitched to inner surface 26 of body 10 and substantially covers forearm section 56 of base 36. Second elevation pad 20 is stitched to inner surface 26 of body 10 and substantially covers upper arm section 54 of base 36. Other coupling arrangements of first and second elevation pads 18, 20 to forearm and upper arm sections 54 56, respectively, such as cementing, taping, Velcro™-like fastening, etc., are contemplated. First and second elevation pads 18, 20 each include first and second beveled edges 72, 74. First beveled edges 72 are positioned toward opposing outer edges 76, 78 of base 36. Second beveled edges 74 are positioned toward intermediate portion 58 of base 36. In an exemplary embodiment, first and second elevation pads 18, 20 each have a thickness of 1.5 inches, a length of 2.5 inches on an inner face 80, 82 and length of 3.0 inches on an outer face 84, 86. First and second elevation pads 18, 20 are configured to align and support elbow 30 above bed surface 12. First and second elevation pads 18, 20 are each made of a single piece of material 88. Inner face 80, 82 of each elevation pad 18, 20 includes a plurality of flat areas spaced apart from each other in two dimensions by a plurality of dimples extending into each elevation pad 18, 20 from the flat areas providing inner face 80, 82 of each elevation pad 18, 20 with a dimpled, flat face. The dimpled face of inner face 80, 82 providing air ventilation to a patient's elbow 30, while providing a soft, flat inner surface without peaks that may harm or irritate some patients, particularly edematous patients. Also, the gripping action of material 88 assists in securely holding elbow 30 in a properly aligned and supported position. Second beveled edges 74 of elevation pads 18, 20 conform to elbow 30 and allow for full contraction and extension of patient's arm. In an alternative exemplary embodiment, device 10 includes one elevation pad connected to and substantially covering base 36. In another alternative exemplary embodiment, device 10 includes one elevation pad connected to base 36, the elevation pad including an opening having a conical or tapered shape configured to receive elbow 30 of the bed patient.

Referring to FIGS. 1, 3 and 4, strap 22 is shown. Strap 22 is an elongate layer of soft, woven fabric having first and second ends 92, 94. First end 92 is stitched to outer surface 66 of body 10. Other means for fastening first end 92 to body 10 such as cementing, taping, etc. are contemplated. An inner surface 68 of strap 22 includes a layer 69 of Velcro™-like soft hook material affixed to strap 22. Strap 22 is configured to wrap around the bed patient's elbow and releasably fasten at second end 94 to covering 40. Layer 69 releasably fastens to the Velcro™-like loop material of covering 40. In an exemplary embodiment, strap 22 has a width of 2 inches. Strap 22 allows device 10 to be securely fastened to all patients thereby providing proper alignment of elbow 30 within body 10. Layer 69 of strap 22 provides a felt-like contact surface with the patient's arm that allows for comfortable, extended wear of device 10 by the bed patient. Alternative strap materials such as plastic, synthetic micro fibers, etc. are contemplated.

Figure 5:
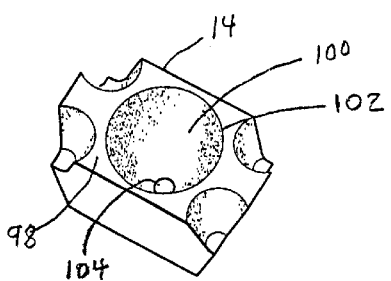
FIG. 5 is a perspective of an auxiliary pad in accordance with an exemplary embodiment of the present invention.
Figure 6:
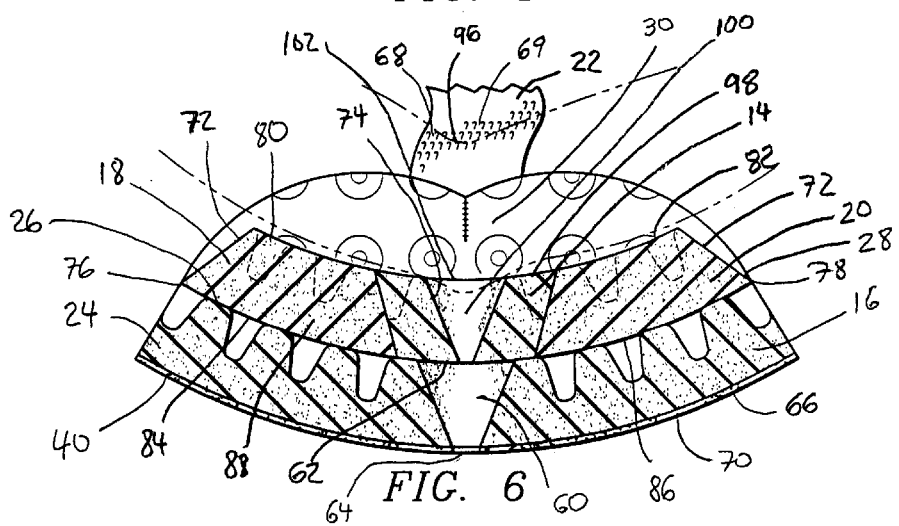
FIG. 6 is a longitudinal cross-sectional view of the elbow protective device taken substantially along lines 2—2 of FIG. 1 further including the auxiliary pad of FIG. 5.

Referring to FIGS. 5 and 6, auxiliary pad 14 is shown. Auxiliary pad 14 is a generally tapered, soft, flexible, compressible and resilient foam insert configured to removably fit between first and second elevation pads 18, 20 and opening 60 of base 36. Auxiliary pad 14 is made of an open-celled, breathable, non-latex, non-allergenic, medical grade foam material such as polyurethane. Auxiliary pad 14 has a flat-faced, dimpled inside surface 98, similar to body 10 and elevation pads 18, 20. Auxiliary pad 14 includes an auxiliary pad opening 100. Auxiliary pad opening 100 having a conical shape, tapered from a first area 102 across inner surface 98 of auxiliary pad 14 to a smaller second area 104 across an outer surface 106 of auxiliary pad 14, wherein first area 102 is larger than second area 104. Auxiliary pad 14 is configured to be optionally and removably inserted between elevation pads 18, 20 to receive and to provide annular support to a portion of elbow 30. Other auxiliary pad opening 100 configurations such as tapered rectangular, tapered oval, tapered triangular etc. are contemplated. In an alternative exemplary embodiment, auxiliary pad opening 100 only partially extends into auxiliary pad 14. Auxiliary pad 14 may be used to provide additional support of elbow 30, when required.

A method of applying device 10 to the bed patient includes the following steps. The method includes releasably securing strap 22 to outer surface 66 of body 10, sliding device 10 under elbow 30 of bed patient, aligning patients elbow with first and second elevation pads 18, 20 and opening 60, grasping first and second segments 92, 94 of strap 22 to pull first and second side panels 32, 34 together, and securing strap 22 by releasably connecting first and second segments 92, 94 to one another. In an exemplary embodiment, strap 22 may be releasably connected to body 10. In an alternative exemplary embodiment, method may include removably inserting auxiliary pad 14 between first and second elevation pads 18, 20 of device 10.

Device 10 is configured to allow one size to fit all bed patient's. This eliminates the need for health service organizations, such as hospitals, nursing homes, care centers, etc. from having to procure and stock multiple sizes of elbow protection devices in order to satisfy their patient's needs. Device 10 is also configured to be machine washable. Further, device 10 is configured to be easily stacked and packaged to facilitate transportation and storage requirements.

While the embodiments illustrated in the FIGURES and described above are exemplary embodiments, it should be understood that these embodiments are offered by way of example only, and various alternatives would be apparent to those of skill in the art. For example, the device may also be provided without elevation pad and auxiliary pads.

What is claimed is:

1. An elbow protection device for an elbow of a bed patient, comprising:

a non-tubular body having first and second side panels connected to and spaced apart by a base having a forearm section an upper arm section and an intermediate section between the forearm and the upper arm sections, the body being made of a flexible, compressible material;

first and second elevation pads connected to the fore arm and upper arm sections, respectively, the base and the first and second elevation pads configured to provide a double layer of support to the forearm and lower portion of the upper arm for supporting the elbow above a bed surface; and an attachment strap connected to the device and configured to secure the body to the elbow.

2. The elbow protection device of claim 1, wherein an inner surface of the base has an indentation extending into the base and positioned between the first and second elevation pads, the indentation configured to receive a portion of the elbow.

3. The elbow protection device of claim 1, wherein the base has an opening extending therethrough, the opening positioned between the first and second elevation pads, the opening tapered from a first area across an inner surface of the base to a smaller second area across an outer surface of the base, the opening configured to receive a portion of the elbow.

4. The elbow protection device of claim 3, wherein the opening is a conical opening.

5. The elbow protection device of claim 1, wherein the body is a circular disk contoured to receive the elbow.

6. The elbow protection device of claim 1, wherein an inner surface of the body includes a plurality of flat areas spaced apart from each other in two dimensions by a plurality of dimples extending into the body from the flat areas.

7. The elbow protection device of claim 1, wherein the first and second elevation pads each include a beveled edge, and an intermediate portion of the base extends between the beveled edges.

8. The elbow protection device of claim 1, further comprising a covering connected to an outer surface of the body, the covering including a friction reducing material for permitting free sliding movement of the device over the bed surface with minimal resistance.

9. The elbow protection device of claim 8, wherein the friction reducing material is a loop material.

10. An elbow protection device for an elbow of a bed patient, comprising:

a body having first and second side panels connected to and spaced apart by a base having a forearm section and an upper arm section, the body being made of a flexible, compressible material;

first and second elevation pads connected to the fore arm and upper arm sections respectively, the base and the first and second elevation pads configured to provide a double layer of support to the forearm and lower portion of the upper arm for supporting the elbow above a bed surface;

an attachment strap connected to the device and configured to secure the body to the elbow: and an auxiliary pad configured to fit between the first and second elevation pads.

11. The elbow protection device of claim 10, wherein the auxiliary pad has an inner face including an indentation, the indentation configured to receive a portion of the elbow.

12. The elbow protection device of claim 10, wherein the auxiliary pad has a pad opening extending therethrough, the pad opening tapered from a first area across an inner surface of the auxiliary pad to a smaller second area across an outer surface of the auxiliary pad, the pad opening configured to receive a portion of the elbow.

13. The elbow protection device of claim 10, wherein the pad opening is a conical opening.

14. An elbow protection device for an elbow of a bed patient, comprising:
   a non-tubular body having a base, the base being made of a flexible, compressible material and configured to support the elbow above a bed surface; and
   a covering connected to an outer surface of the body, the covering including a friction reducing material having a plurality of loops for permitting free sliding movement of the device over the bed surface with minimal resistance.

15. The elbow protection device of claim 14 further comprising an attachment strap removably connected to the device and configured to secure the body to the elbow.

16. The elbow protection device of claim 14, further comprising an attachment strap having a first portion connected to the body and a second portion of strap releasably connectable to the covering, the strap configured to releasably secure the body to the elbow.

17. The elbow protection device of claim 16 further comprising a soft hook material connected to an inner side of the strap, the hook material releasably connectable to the loop material of the covering.

18. The elbow protection device of claim 14, wherein the base has an opening extending therethrough, the opening positioned between the first and second elevation pads, the opening tapered from a first area across an inner surface of the base to a smaller second area across an outer surface of the base, the opening configured to receive a portion of the elbow.

19. The elbow protection device of claim 14, wherein an inner surface of the body includes a plurality of flat areas spaced apart from each other in two dimensions by a plurality of dimples extending into the body from the flat areas.

20. An elbow protection device for an elbow of a bed patient, comprising:
   a non-tubular body being made of a flexible, compressible, breathable foam material, the body including an inner surface having a plurality of flat areas spaced apart from each other in two dimensions by a plurality of dimples extending into the body from the flat areas, the body contoured to receive the elbow and configured to support the elbow above a bed surface.

21. The elbow protection device of claim 20, wherein the dimples extend into the body by at least one quarter of the distance from the inner surface of the body to an outer surface of the body.

22. The elbow protection device of claim 20 further comprising first and second elevation pads connected to the body, the body and the first and second elevation pads configured to provide a double layer of support to the forearm and lower portion of the upper arm for supporting the elbow above a bed surface.

23. The elbow protection device of claim 20, wherein the base has an opening extending therethrough, the opening positioned between the first and second elevation pads, the opening tapered from a first area across an inner surface of the base to a smaller second area across an outer surface of the base, the opening configured to receive a portion of the elbow.

24. The elbow protection device of claim 20, further comprising a covering connected to an outer surface of the body, the covering including a friction reducing material for permitting free sliding movement of the device over the bed surface with minimal resistance.

25. The elbow protection device of claim 24, wherein the friction reducing material is a loop material.

26. An elbow protection device for an elbow of a bed patient, comprising:
   a non-tubular body having first and second side panels connected to and spaced apart by a base, the body being made of a flexible, compressible material, the base having an opening extending therethrough, the opening substantially continuously tapered from a first area across an inner surface of the base to a smaller second area across an outer surface of the base, the opening configured to receive a portion of the elbow.

27. The elbow protection device of claim 26 further comprising first and second elevation pads connected to the body, the body and the first and second elevation pads configured to provide a double layer of support to the forearm and lower portion of the upper arm for supporting the elbow above a bed surface.

28. The elbow protection device of claim 27, wherein the base has an opening extending therethrough, the opening positioned between the first and second elevation pads, the opening tapered from a first area across an inner surface of the base to a smaller second area across an outer surface of the base, the opening configured to receive a portion of the elbow.

29. The elbow protection device of claim 26, further comprising a covering connected to an outer surface of the body, the covering including a friction reducing material for permitting free sliding movement of the device over the bed surface with minimal resistance.

30. A method of applying an elbow protection device for supporting a bed patient's elbow above a bed surface, the method comprising the steps of:
   sliding a non-tubular body of the device under the elbow of the bed patient, the body made of a flexible, compressible support material;
   placing the bed patient's elbow on first and second elevation pads connected to an inner surface of the body thereby providing a double layer of support for the portions of the elbow in contact with the first and second elevation pads;
   aligning the elbow with an opening within a body of the device and the first and second elevation pads;
   grasping a first end of a strap, the strap connected to the body at a second end;
   wrapping the strap around the elbow; and
   releasably connecting the strap to the body.

31. A method of applying an elbow protection device for supporting a bed patient's elbow above a bed surface, the method comprising the steps of:
   sliding a body of the device under the elbow of the bed patient;
   placing the bed patient's elbow on first and second elevation pads connected to an inner surface of the body;
   aligning the elbow with an opening within a body of the device and the first and second elevation pads;
   grasping a first end of a strap, the strap connected to the body at a second end;
   wrapping the strap around the elbow;
   releasably connecting the strap to the body; and
   removably inserting an auxiliary pad between the first and second elevation pads of the body for further supporting the elbow of the bed patient above a bed surface.

* * * * *